US012779108B2

(12) United States Patent
Casteleyn et al.

(10) Patent No.: US 12,779,108 B2
(45) Date of Patent: Nov. 3, 2026

(54) PACKAGED NEEDLE ASSEMBLY

(71) Applicant: Terumo Europe NV, Leuven (BE)

(72) Inventors: Pieter Nico Jan Casteleyn, Herent (BE); Hans Valkenaers, Booischot (BE); Ludo Daniels, Tongeren (BE); Christian Fripon, Haasrode (BE)

(73) Assignee: Terumo Europe NV, Leuven (BE)

( * ) Notice: Subject to any disclaimer, the term of this patent is extended or adjusted under 35 U.S.C. 154(b) by 0 days.

(21) Appl. No.: 18/866,356

(22) PCT Filed: May 17, 2023

(86) PCT No.: PCT/EP2023/063329
§ 371 (c)(1),
(2) Date: Nov. 15, 2024

(87) PCT Pub. No.: WO2023/222800
PCT Pub. Date: Nov. 23, 2023

(65) Prior Publication Data

US 2025/0345510 A1 Nov. 13, 2025

(30) Foreign Application Priority Data

May 18, 2022 (EP) .................................... 22174090
May 18, 2022 (EP) .................................... 22174144

(51) Int. Cl.
*A61M 5/00* (2006.01)
*A61L 2/20* (2006.01)
(Continued)

(52) U.S. Cl.
CPC ............... *A61M 5/002* (2013.01); *A61L 2/20* (2013.01); *A61M 5/3202* (2013.01); (Continued)

(58) Field of Classification Search
CPC .. A61M 5/002; A61M 5/3202; A61M 5/5086; B65D 2203/00; A61L 2103/15; A61L 2/20
(Continued)

(56) References Cited

U.S. PATENT DOCUMENTS 3,149,717 A 9/1964 Castelli
10,518,943 B2 * 12/2019 Gelov .................... B65D 35/08
(Continued)

FOREIGN PATENT DOCUMENTS

EP 0517121 A2 12/1992
EP 0517121 A3 3/1993
WO 2016108869 A1 7/2016

OTHER PUBLICATIONS

International Search Report and Written Opinion—PCT/EP2023/063329—mailing date Nov. 23, 2023.

*Primary Examiner* — Steven A. Reynolds
(74) *Attorney, Agent, or Firm* — Banner & Witcoff, Ltd.

(57) ABSTRACT

The present disclosure concerns medical equipment and, more specifically, a hard case packaging product for sterile packaging of a needle assembly, a packaging product, and a packaging method. The hard shell product comprises a case (2) and a cap (3) configured to in an engaged condition defining an enclosure (4) for the needle assembly (100), whereby one or more radial channel is formed that extends in a longitudinal direction between the overlapping sidewall sections and that provide a gas passage to the enclosed volume. In a preferred embodiment, the cap comprises at least a first (31) and a second cap part (32) that are by one or more interconnection member (33) configured to break by displacing the second cap part (32) with respect to the case (2) while retaining a coupled connection between the first cap part (31) and the case (2).

20 Claims, 5 Drawing Sheets

(51) Int. Cl.

| | |
|---|---|
| ***A61M 5/32*** | (2006.01) |
| ***A61M 5/50*** | (2006.01) |
| ***B65B 55/02*** | (2006.01) |
| *A61L 103/15* | (2026.01) |

(52) U.S. Cl.
CPC ........... *A61M 5/5086* (2013.01); *B65B 55/02* (2013.01); *A61L 2103/15* (2026.01); *A61M 2205/583* (2013.01); *A61M 2209/06* (2013.01)

(58) Field of Classification Search
USPC ................................................ 206/365, 459.1
See application file for complete search history.

(56) References Cited

U.S. PATENT DOCUMENTS

| | | | | |
|---|---|---|---|---|
| 11,207,472 | B2 * | 12/2021 | Rini | A61M 5/46 |
| 2002/0130100 | A1 * | 9/2002 | Smith | B01L 3/50825 220/259.2 |
| 2014/0048433 | A1 * | 2/2014 | Dasbach | A61M 5/3213 206/366 |
| 2014/0135713 | A1 * | 5/2014 | Domonkos | A61B 17/3496 29/525 |
| 2019/0224405 | A1 | 7/2019 | Guillaume et al. | |
| 2020/0365061 | A1 * | 11/2020 | Shinkle | G09F 3/0292 |
| 2023/0230509 | A1 * | 7/2023 | Young | B32B 7/12 40/638 |

* cited by examiner

PACKAGED NEEDLE ASSEMBLY

CROSS-REFERENCE TO RELATED APPLICATIONS

This application is a U.S. National Stage application under 35 U.S.C. § 371 of International Application PCT/EP2023/063329 (published as WO 2023/222800 A1), filed May 17, 2023, which claims the benefit of priority to Application EP 22174144.0, filed May 18, 2022, and to Application EP 22174090.5, filed May 18, 2022. Benefit of the filing date of these prior applications is hereby claimed. Each of these prior applications is hereby incorporated by reference in its entirety.

TECHNICAL FIELD AND BACKGROUND

The invention generally relates to medical equipment and, more specifically, to a hard case packaging product for sterile packaging of a needle assembly for use in medical injection equipment, a packaging product, and to a packaging method.

Safety needle assemblies are widely known and used. Typically, a safety needle assembly comprises a hub having a proximal end for connecting with a syringe. Prior to the use the assembly is stored in a package under sterile conditions.

Blister packaging solutions are well known. Upon use the user, e.g. a paramedical person partially opens the blister to make the hub free, and then holds the assembly at the packaging to connect the hub to the syringe to avoid contamination or a possible sterility breach of the needle assembly. Then, the user further removes the packaging to make the safety needle assembly free. This process is rather complex and can be prone to user error.

While enabling storage of sterilized products, blister packages are generally less compatible with high speed automated packaging processes. For example, blister packages comprise flexible or deformable portions that are difficult to grip by an automated pickup or assembly tool. Additionally blister packages can be easily deformed or damaged by automated handling, so that the packaging process is generally slow and/or requires one or more manual handling steps. Further, the blister packages tend to be comparatively bulky, which is disadvantageous in terms of storage and transport.

WO2016108869A1 describes a sorbent container with a first member and a second member that, when attached, form a closed container with first and second internal spaces. EP0517121A2 shows a vented cap and capillary tube assembly, which includes a capillary tube with a bore extending through it and a cap slidably mounted to one end of the tube, with vent grooves to allow air to escape when in a certain position. U.S. Pat. No. 3,149,717A describes a needle container where the cap tightly fits into the open bore of the hub to maintain sterility, and the leading end of the closure portion extends well into the container bore to remain sterile. US2002130100A1 discloses an injection molded assembly that can seal threaded or non-threaded containers using a double cap concept with pressure responsive convex sealing.

Hard case packaging products may in part mitigate disadvantages as to machine handling. However, the comparatively more rigid enclosure disadvantageously hinders sterilization of the packaged product by limiting access to radiative and/or fluid sterilization agents.

Additionally, and in particular for hard case packaging products, there remains a need to provide tamper proof packaging solutions to reassure an end user of product quality, in to reassure sterility of the product by indicating that the package has not been opened previously.

Accordingly there remains a need for packaging solutions that eliminate or at least mitigate one or more of the above disadvantages.

SUMMARY

Aspects of the present disclosure relate to a hard shell packaging product. In particular to a hard case product for packaging a needle assembly.

As will be explained in more detail herein below the packaging product as described herein advantageously provides a packaging product that is comparatively compact; that offers improved automated machine handling characteristics; that offers improved ease of user-operation, e.g. in connecting a syringe to the hub; and/or that includes tamper proofing measures; while enabling sterilization of the packaged product by a gaseous desinfectant.

The hard shell packaging product comprises at least a case and a cap that are mutually configured to engage, preferably by sliding one over the other over a predesigned engagement distance, wherein the case and the cap comprise circumferentially overlapping sidewall sections. The hard shell packaging product further comprises, in an engaged condition, one or more radial channel. The radial channel extends in a longitudinal direction between the overlapping sidewall sections so as to provide one or more channel that allows or promotes gas passage to a packaged product contained within an enclosed volume as defined by cap and case. Providing a gas passage to the enclosed volume, advantageously allows sterilizing the packaged product, e.g. the needle assembly. As will be detailed herein below the packing product advantageously allows gas access to the needle assembly for sterilization by a gaseous agent while being enclosed by the cap and the case. Preferably, the channel(s) form the only passage between the interior volume and ambient. By having the channels extend over a distance, e.g. the predesigned engagement distance, between an inner face of the cap and an exterior face of the case (or vice versa) re-contamination of the needle assembly by air-borne infectants is mitigated.

Preferably, the hard shell packaging product comprise one or more single use means for securing the cap relative to the case. The single-use securing means breaks or deforms irreversibly upon opening the package. As such the single-use securing means provides a visual indication of a breach of sterile conditions, e.g. by an accidental or unauthorized prior opening of the packaging product. As will be detailed in further detail herein the single-use securing means can be embodied by one or more pairs of mutually engaging (e.g. snap lock) members provided along the cap and the case. Alternatively, or in addition, on the single use securing means can be embodied by one or more interconnection members (e.g. bridging members that interconnect respective parts of the hard shell packaging product and that irreversible deform, e.g. break, upon exceeding a threshold force and/or threshold strain. It will be appreciated that the single use securing means can advantageously further prevent re-closing or re-assembly of cap and case after an initial assembly.

The hard shell product is preferably embodied so that the cap comprises at least two parts, including a first cap part that comprises one or more means for securing to the case; and a second cap part that is connected to the first cap part by one or more interconnection member. The interconnection member is configured to irreversibly break by displacing the second cap part with respect to the case while retaining a coupled connection between the first cap part and the case. Thus, the package can be opened by removing the second cap part, without releasing the first cap part from the case. The remaining interconnection means (broken or otherwise deformed) can advantageously provide a visual indication of removal of the second cap part while improving tamper proofing by preventing re-closure of the packaging product once opened. Additionally, the interconnection member(s) can advantageously define a force, e.g. torque and/or linear pull force, required to open the package.

The first cap part, the second cap part, and the interconnection members, are preferably integrally formed as a single piece, e.g. by injection moulding. This mitigates a potential of tampering, relaxes manufacturing conditions, and/or reduces an overall area of contact interfaces that may be occluded for access by gaseous disinfectants.

In preferred embodiments, the overlapping sidewalls are separated across a gap by one or more spacers. The spacers can advantageously define a cross section of the gap. The spacers further advantageously provide contact force and/or friction between cap and case so as to provide a snug or secure fit.

The spacers can be provided by one or more protrusion, e.g. rib(s), pip(s), domes, or other shaped protrusions, that extend from at least one of an inner face of the overlapping wall section of the cap towards a corresponding overlapping wall section of the case, and an exterior face to the circumferentially overlapping wall section of the case towards a corresponding wall section of the cap.

Advantageously, the overlapping wall sections can contact each other exclusively via the one or more protrusion. This reduces an overall area of surfaces (surface in flush contact) that are occluded from contact by gaseous disinfectants.

To prevent or at least hinder removal of the first cap member form the case after initial assembly the one or more of the interconnection member for securing the first cap part to the case can comprise interlocking elements, e.g. members configured to snap into a locked position such as a hook and slot or one or one more protrusion and corresponding socket members. Preventing or at least hindering removal of the first cap member form the case after initial assembly further improves tamper protection.

It will be appreciated the interconnection members are preferably configured to break at a force smaller than a snap out force for releasing the interlocking elements from the locked position.

Preferably, the case is further configured to restrict rotational freedom of the needle assembly while in the case. Rotation of the needle assembly along a longitudinal axis within the case (e.g. in a direction along a central axis of the case) can hinder attachment/coupling of a syringe to the hub of the needle assembly. Restricting rotation of the needle assembly within the case can in particular avoid user error when the hub is configured for coupling to a syringe by a rotational or screw-on motion (e.g. a Luer-lock). Restricted rotational motion can be provided by a case that comprises one more engagement faces configured to engage with one or more faces of the needle assembly, such as the hub, the sleeve, and/or, the needle protector. Accordingly, the case can advantageously be provided with one or more engagement members (such as slots, pips or ribs), dimensioned and positioned to engage an external face of the needle assembly upon rotation. Alternatively, or in addition, the inner volume may be shaped to prevent rotation of the needle assembly, e.g. by a cross-sectional shape (e.g. rectangular).

To prevent unintentional damaging the one or interconnection member(s) (e.g. bridges) that interconnect the first and the second cap parts, e.g. during (machine) assembly of the cap to the case the first cap part is preferably provided with one or more push or grip members. The grip or push member provides a point of contact for an operator or machine grip to provide a force to assemble the cap onto the case. Typically, the grip or push member extends outwardly from an exterior side face of first cap part. Alternatively, or in addition, grip may provide by one or more slots or trenches. The grip or push member(s) thus protect the comparatively fragile interconnection members between first and second part from damage during assembly of the cap onto the case.

Preferably, the one or more push member overlaps at least in part with the means for securing the first cap part to the case. Overlapping the push member with the means for securing the first cap part to the case limits access to an interlocked connection formed between case and cap once and thus builds upon further increasing tamper protection.

To increase external manual grip, e.g. for disconnecting the cap from the case, one or more of the case and the second cap part (preferably both) can be provided with one or more external grip members.

Alternatively, or in addition, the hard shell packaging product preferably comprises one or more retention member that restricts, displacement of the needle assembly along the longitudinal direction within the case. The retention member confines the needle assembly to the case even with the cap in an open condition until a retaining force is exceed, e.g. by an intentional user-applied pulling force. Thus accidental drop out can be avoided. The retention member is typically provided along an internal sidewall of the case, such as a circumferential rim, that engage with the needle assembly.

As an alternative or in addition to one or more of the single use means for securing the cap to the case an adhesive label, can be applied. The label fixes the respective parts, preferably by extending circumferentially across a boundary between the cap and the case, and/or between the cap parts. Opening the packaging product results in tearing the label. Formed tear marks, serve as a visual indicator of opening of the hard shell packaging product. To reduce a user-force required to break the seal the label preferably comprises a plurality of perforation lines that extend across the boundary between the cap and the case. Provision of the perforation lines was found to advantageously further increase visibility of tear marks.

Accordingly, in some embodiments, the packaging product comprises a label that adheres to an outer face of both the case and the cap, whereby the label has a dimension along a first direction that spans at least a portion of a perimeter of the packaging product at a position of the gap, and whereby the label, along a second direction, is dimensioned to cross the gap thereby fixing the case relative to the cap, wherein the label includes a perforated section extending in a direction along the first dimension of the label, the perforated section comprising a plurality of perforation lines arranged at an inclined angle relative to the gap, the perforated lines having a first end one that terminates beyond the edge of the case at the base of the collar and a second end that terminates beyond the edge of the cap across the gap. An angle of 20-40 degrees, preferably about 30 degrees was confirmed to provide an optimum visibility of tear marks while retaining an overall structural integrity of the label that allows automated application without premature tearing of the label.

Further or additional aspects concern a cap and a case (e.g. a kit) for assembly into a hard shell packaging product, such as the hard shell product for packaging a needle assembly as disclosed herein, the cap and the case defining an enclosure for a product to be stored in a coupled configuration, wherein the case and cap are configured to, in the coupled configuration, provide circumferentially overlapping sidewall sections and wherein one or more radial channel is provided that extends in a longitudinal direction between the overlapping sidewall sections so as to provide a gas passage to the needle assembly.

Preferably, and for reasons described in relation to the packaging product, the cap preferably comprises at least a first cap part comprising means for the securing to the case; and a second cap part that is connected to the first cap part by one or more interconnection member members configured to break by displacing the second cap part with respect to the case while retaining a coupled connection between the first cap part and the case.

Even further or additional aspects relate to a packaged needle assembly. The needle assembly is enclosed by the packing product or the cap and the case as disclosed herein.

Yet further or additional aspects relate to a method of packaging a product, preferably a needle assembly. The method comprises: closing a storage volume around a product to be packaged by coupling the case and the cap as disclosed herein. The method may comprise a further step of exposing the product to a gaseous disinfectant. Suitable gaseous disinfectant include but are not limited to ethylene oxide, nitrogen dioxide, steam, ozone, and/or peroxides such as vaporized hydrogen peroxide. Advantageously the step of exposing the product to a gaseous disinfectant can be performed after coupling the cap and the case (post packaging), e.g. just after packaging and/or even after prolonged storage such as just prior to an intended opening of the package.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Figure 1:
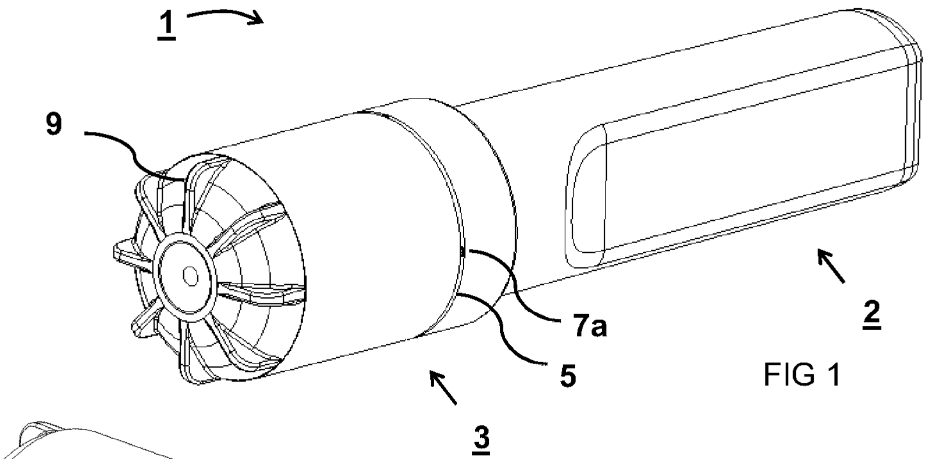
FIG. 1 provides a perspective view of a hard shell packaging product in closed condition.

Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise.

As used herein the term needle assembly may be understood as relating to needle assembly comprising a hub having a proximal end for connecting with a syringe extending in a proximal area of the hub; and a needle longitudinally extending from a distal end of the hub in a distal area of the hub.

The needle assembly typically comprises at least a canula (also referred to as needle) that extends from a needle hub for receiving a corresponding counterpart of a syringe. Preferably, the needle assembly is a safely needle assembly comprising a protector that is typically embodied as a longitudinally extending sleeve that can be engaged over the needle, and that at an end there of can be removably connected to the hub, and a sheath that is pivotally connected to the hub. The sheath typically has two side walls connected by a back wall defining a receiving space therebetween for receiving the needle. The sheath is pivotable between a starting position in which the sheath is free from the needle, between a use position in which the sheath is pivoted away from the needle and the needle is exposed, and between a locked position in which the sheath is locked to secure the needle into the receiving space. In the locked position, the sheath protects the needle, after its use, against unintended contact, contamination, needlestick injury etc. In the locked position, the needle is received in the receiving space of the sheath to be enclosed by the sheath, and as such, to cover the needle.

Although not exclusively, the packaging product is of particular benefit for a safety needle assembly, such as a safety needle assembly described in full detail in PCT/EP2021/063205, which is hereby incorporated by reference.

The safety needle assembly preferably comprises a hub having a proximal end for connecting with a syringe extending in a proximal area of the hub; a needle longitudinally extending from a distal end of the hub in a distal area of the hub; a sheath pivotally connected to the hub, the sheath having two side walls connected by a back wall defining a receiving space therebetween for receiving the needle; wherein the sheath is adjustable between a starting position in which the sheath is substantially positioned in the distal area of the hub, between a use position in which the sheath is substantially positioned in the proximal area of the hub, and between a locked position in which the sheath (protector) is locked to secure the needle into the receiving space; wherein in the starting position the sheath is longitudinally extending from the hub, wherein the hub is provided with at least one first cooperating element and the sheath is provided with at least one second cooperating element, wherein, in the locked position of the sheath, the first and the second cooperating elements are engaged to each other for locking the sheath, characterized in that, in the starting position, the first and second cooperating elements are in contact with each other for defining the starting position of the sheath.

By providing the sheath longitudinally extending from the hub in the starting position, the footprint of the safety needle assembly in the starting position, thus for packaging purposes, becomes much less, allowing different types of packaging and/or more efficient packaging and/or transport and/or storage. For example, which such a reduced footprint, a hard case packaging may be considered, allowing automated handling of the packed safety needle assembly. Whereas, automated handling of blister packed assemblies is practically not possible, resulting that the blister packed assemblies need to be collected manually in a box for transport and storage. This limits the speed of assembly lines. By providing the sheath in a longitudinally extended position from the hub in starting position, a more compact arrangement of the safety needle assembly can be obtained, allowing a hard case packaging. Such hard case packaging can be handled automated allowing the speed of the assembly lines to increase, thus allowing a more efficient production, packaging, transport and/or storage of the safety needle assembly. Also, by using a hard cap, the way of working for preparing the needle assembly to use remains unchanged. This is advantageous for the user as he can follow the procedure he is used to. When removing the cap of the hard case, the hub of the needle assembly becomes exposed and can be connected to the syringe without compromising the sterility and avoiding possible contamination. When connected to the syringe, the hard case can be removed from the needle assembly and the sheath can be pivoted to the use position to make the needle with syringe ready for use.

The hard case preferably comprises, or essentially consists of, a medical grade composition, preferably a plastic composition that can be injection molded, such as polypropylene.

The invention is described more fully hereinafter with reference to the accompanying drawings, in which embodiments of the invention are shown. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

Figure 2A:
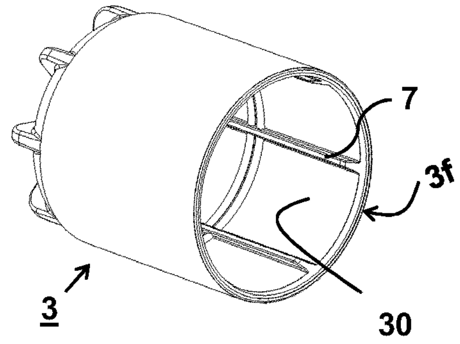
FIGS. 2A and 2B provide perspective views of a cap and a case in an open condition.
Figure 2B:
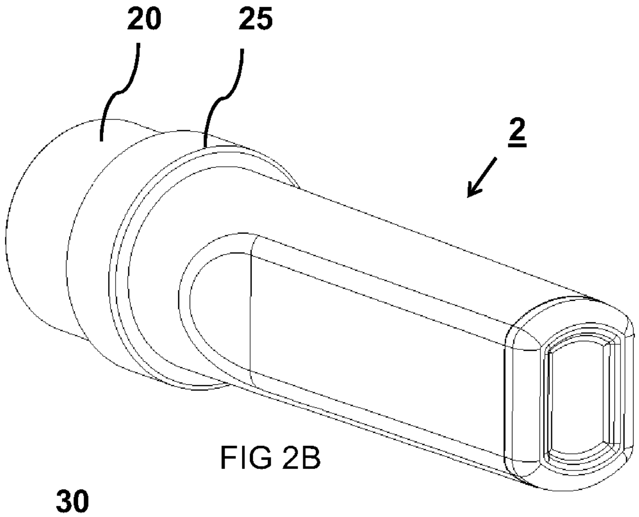

FIGS. 1, 2A and 2B provide a perspective view of a hard shell packaging product 1 in closed (FIG. 1) and open condition (FIG. 2A-B). As shown the hard shell packaging product 1 comprises at least two parts: a case part 2 and a cap part 3. The case and/or cap parts may comprise a flat portion (e.g. as shown). This flat portion prevents a rolling motion of the product, e.g. along a table top. The cap 3 and case 2 can be slidingly engaged, e.g. as illustrated in FIG. 2A-B to a closed condition. Note that sidewall sections 20 and 30 circumferentially overlap. To this end an inner dimension of the cap is configured to be slightly larger than an outer dimension of the case, or vice versa. The closed hard shell packaging product defines an interior volume for storing a needle assembly. As will be elaborated in further detail with reference to FIGS. 2A and 2B the hard shell packaging product 1 comprises a channel 5 that extends in longitudinal direction between the overlapping sidewall sections and that provides a gas passage to the enclosed volume. To this end spacers 7 are provided between the overlapping sidewall sections.

Additionally the spacers, indicated as longitudinally extending ribs, further advantageously provide contact force and/or friction between cap and case so as to provide a snug or secure fit. To facilitate removal of the cap and/or case can be provided with one or more external members for manual grip, such as the ribs 9 indicated in FIGS. 1 and 3.

It will be appreciated that the spacers may be provided to one or more of an the interior/exterior faces of the cap, respectively the case. Likewise it will be appreciated that the term spacer also includes other geometries than the indicated ribs, including but not limited to pips (domes).

Figure 3:
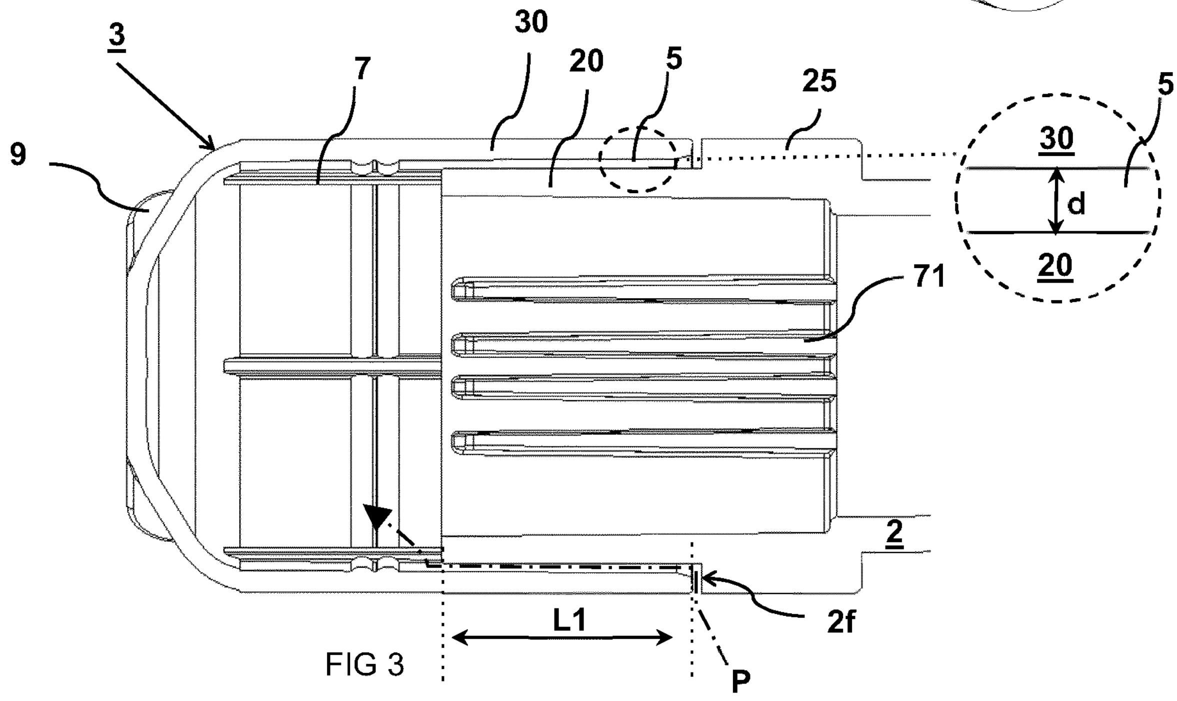
FIG. 3 provides a detail cross-section side view of a cap and a case in a closed condition.

As can be seen in more detail in FIGS. 2A and 3 the spacers can advantageously define a cross-sectional dimension of the channel. The channel length L can be understood as being largely defined by an overlap distance between cap and case. The length L1 of the overlap is generally ≥2 mm. The longer the overlap the more complex the pathway for ingress of contaminants to ingress. In principle the overlap can be larger. The longer the overlap the more stable the cap can be positioned onto the case. For example, the overlap L1 can be up to about 20 mm, e.g. in a range of 2-20 mm or in a range of 3-10 mm. Prevention of re-contamination is believed to relate to the channel providing a stagnant air. An overlap of 2 mm was found to prevent re-contamination. In practice the overlap length L1 is between 5 and 10 mm, e.g. about 8 mm. A range between 5 and 10 mm was confirmed to be an optimum between compactness and stability of the cap onto the case. The width of the channel (distance between opposing sideways) is preferably as thin as possible while allowing gas passage. Typically, the distance between opposing sideways 'd' is less than 1 mm. In principle the separation can be larger, e.g. up to 2 or even 3 mm or more. The thinner channel the compacter the packaging product can be. Preferably, the separation 'd' is ≤0.5. More preferably, d≤0.3 mm, e.g. about 0.2 mm. The wider the channel the larger the access for potential recontamination and the less compact the packed product. A separation of about 0.05 mm was found sufficient.

In a preferred embodiment, e.g. as shown the protrusions for the exclusive contact between opposing sidewall faces of the case and the cap. This limits the area of flush contact between cap and case to essentially point or line contacts as defined by the protrusions.

Figure 4A:
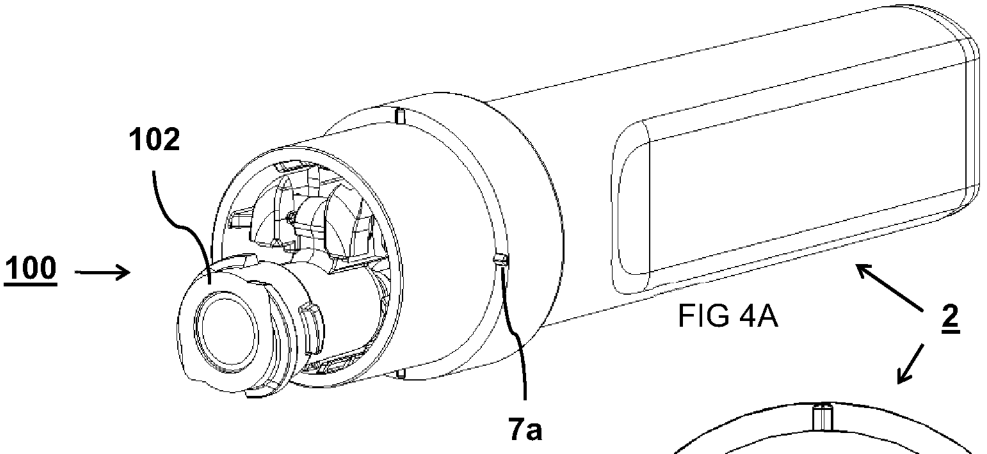
FIGS. 4A and 4B provide a perspective and a plan view of a case and a needle assembly.

In some embodiments, e.g. as shown in FIGS. 1 and 4A one or more further spacers 7*a* are provided between opposing faces of the cap 3*f* and the case, e.g. a face 2*f* of collar 25, to assure an axial clearance between cap and case in closed condition, e.g. as indicated in FIGS. 1 and 3.

Figure 4B:
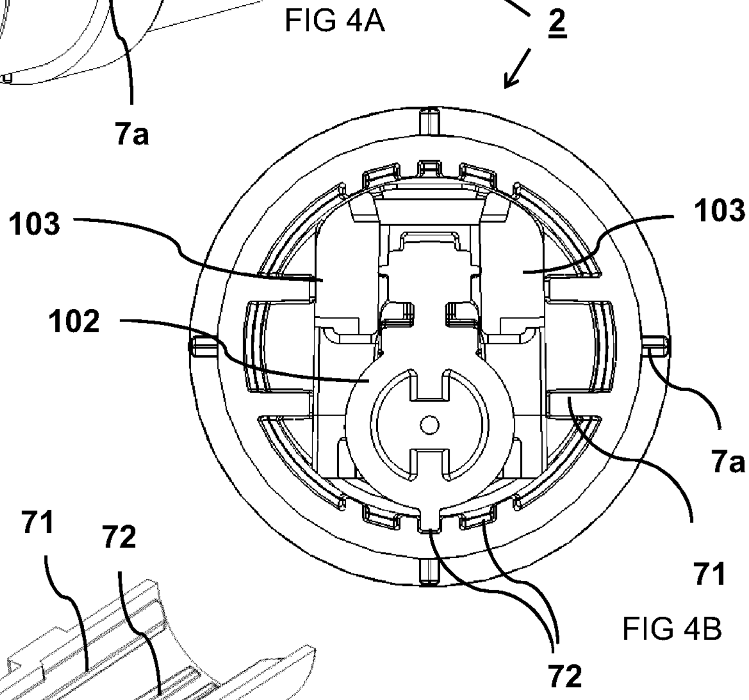

FIG. 4A provides a perspective view of a needle assembly 100 inserted along its longitudinal axis within a case 2. FIG. 4B provides the corresponding plan view. Preferably, a terminal portion of the hub 102 protrudes out of the case after removal of the cap.

Figure 5A:
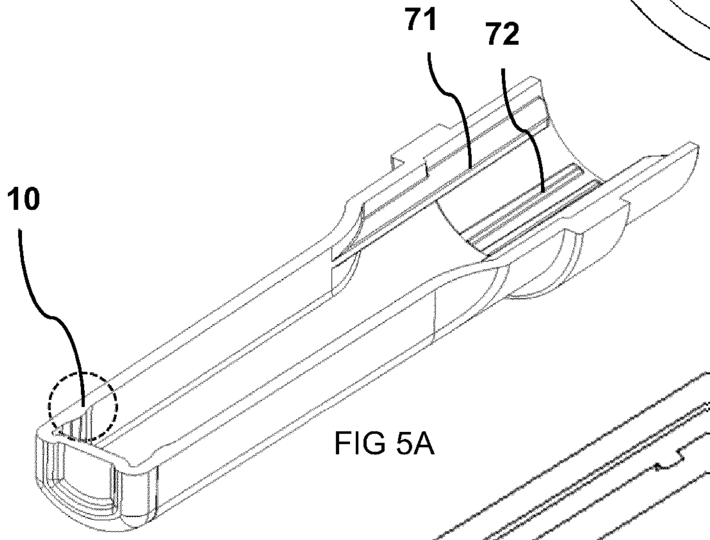
FIGS. 5A and 5B provide cross-section perspective detail views of a case.

To prevent internal rotation of the needle assembly 100 within the case one or more inwardly extending ribs 71 or slots 72 can be provided (e.g. as indicated in FIGS. 4B, 5A, and 3) that engage with the needle assembly 100, e.g. with a needle guard 103 and/or with the hub 102 as indicated).

Alternatively, or in addition, internal rotation of the needle assembly 100 can be mitigated by an internal cross sectional geometry of the case.

Figure 5B:
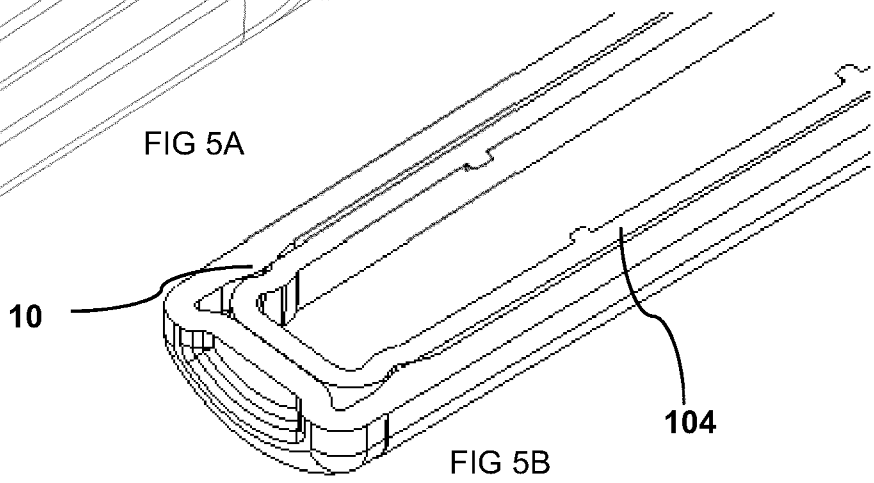
Figure 6:
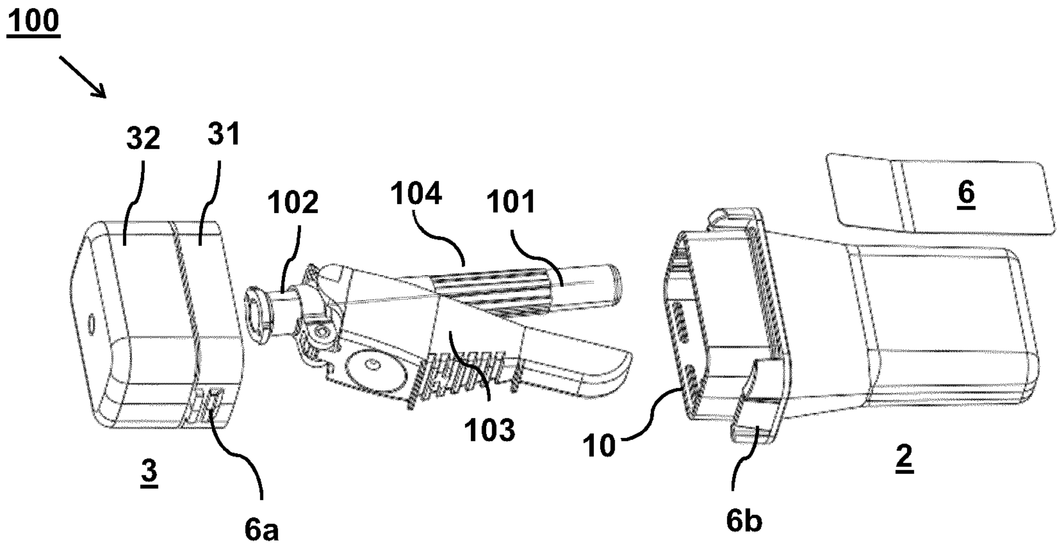
FIG. 6 provides a perspective view of packaging a needle assembly.

Preferably, the case of the hard shell packaging product comprises one or more retaining member. The retaining member is configured to retain the needle assembly 100 in position within the case even when the cap is removed. The needle assembly 100 can be removed by applying a pre-defined minimum extraction force, e.g. by pulling on the hub. FIGS. 5A and 5B depict a case 2 comprising a retention member 10 that is embodied as an inwardly extending protrusion that engages with a corresponding slot provided along the sleeve 104 of the needle assembly to prevent accidental release or drop out of the needle assembly 100 even is the case. FIG. 6 depicts an embodiment wherein the retention member 10 is provided as a plurality of ribs that engage with an edge of the hub 102 and/or the needle guard 103 to prevent accidental release or drop out of the needle assembly 100 even is the case.

The hard shell packaging product can advantageously be shaped to closely follow an outer geometry of the needle assembly 100. This provides a compact packaging solution. In some embodiments, an overall shape of the hard shell packaging product can resemble a cylindrical shape. Other shapes are also possible. For example, a hard shell packaging product 1 having a rectangular cross section, e.g. as shown in FIGS. 6-11.

FIG. 6 provides a perspective view of a needle assembly and hard shell packaging product comprising a case and cap having improved tamper protection features while retaining post-assembly sterilization aspects.

As shown in FIG. 6, the cap comprise a first part 31 and a second part 32. As will be clarified in further detail with reference to FIGS. 7A, 7B and 10, the parts are connected to each other (at least initially) by one or more single use interconnection member 33. The cap can be understood as a segmented cap that includes a top cap part and a circumferential skirt.

Upon assembly of the cap onto the case the skirt as well as part 30 of the second cap part overlap with a sidewall of the case. As indicated in more detail in FIG. 8 a channel 5 is formed between overlapping sidewall sections of the case and the cap. Similar as described in relation to FIG. 3 a gas passage P is formed in a space between opposing faces 21*f* and 31*f* of the case and the cap. The separation, gap 'g', between the first and second cap parts provides access to the gas passage.

Overlap L2 between case and the second cap part is preferably as small as possible while retaining a length sufficient to provide a stagnant air path. The shorter the overlap the lower a potential to re-position the second cap part after an initial opening. As described before the minimum overlap be can as low as 2 mm. Typically the overlap L2 between case and second cap part is in a range of 3-5 mm, e.g. about 3.5 mm. The separation distance ('d', see FIG. 3) between opposing sidewalls is preferably is less than 1 mm, more preferably ≤0.5, most preferably ≤0.3 mm, e.g. about 0.2 mm.

Figure 8:
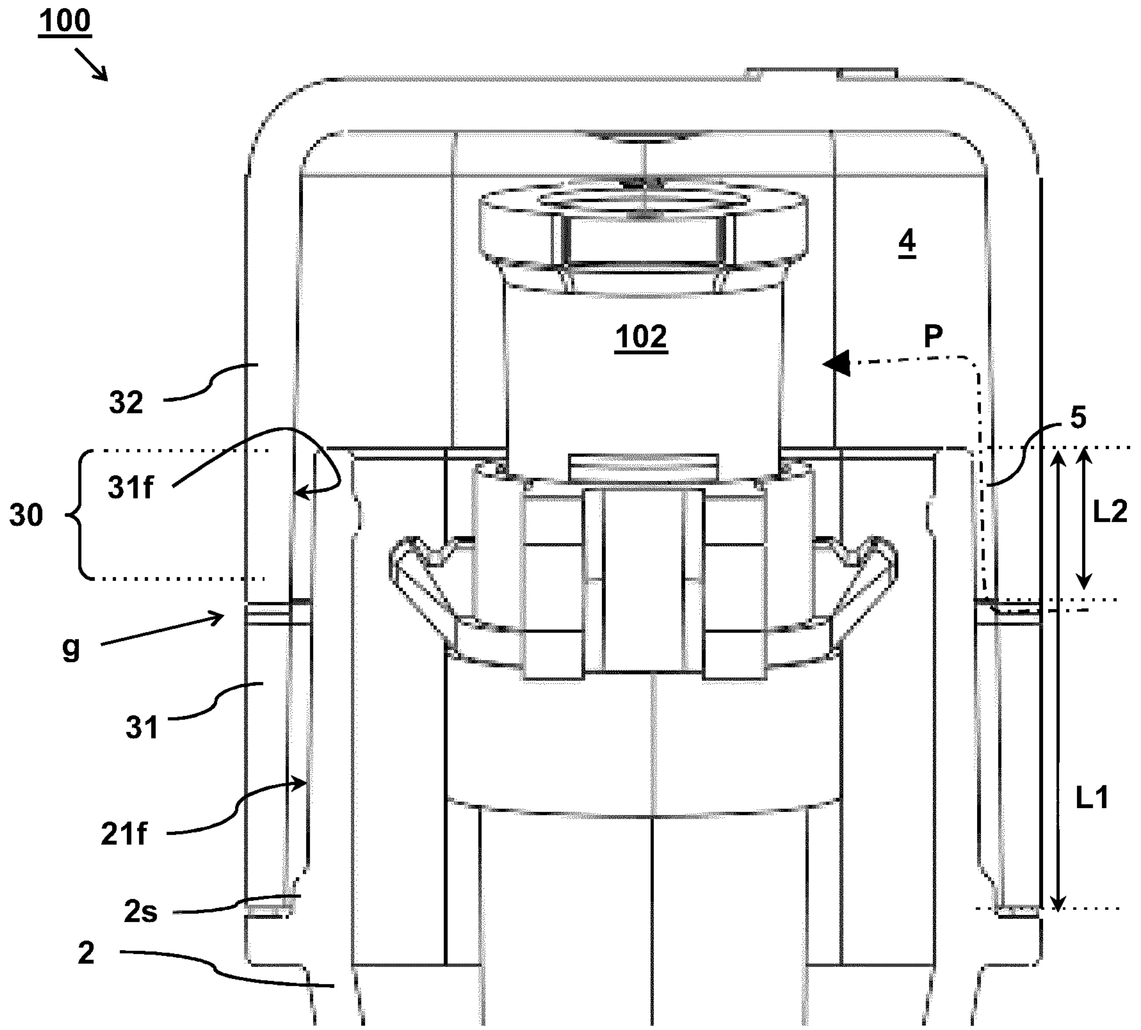
FIG. 8 provides a cross section detail side view of a packaged needle assembly.

To provide a snug fit between cap and case and/or to define a cross-section dimension of the gas passage ribs or protrusions can be provided to the cap and/or case (not shown for clarity). To further lower a lower a potential to re-position the second cap part after an initial opening, the ribs are preferably provided exclusively to the first cap part and/or to sections of the case sidewall that engage the second cap part. Most preferably, the spacing between opposing faces of the cap and case sidewalls 21*f*,31*f* is be defined by a separator 2*s*, e.g. a circular protrusion, that is provided between the case and an inner face of the first cap part 31, e.g. a circular rim 31 as shown in FIG. 8.

Cap and case be fixed to each other by one or more interlocking interconnection means 6. Returning FIGS. 6, 7A, and 7B it will be appreciated that an initial engagement of interconnection member 6*a* (depicted as a slot) that is provided to the first cap part 31 with interconnection member 6*a* (depicted as a clip) that is provided to the second cap part 31 forms an interlocked connection that couples the cap to the case.

Figure 7A:
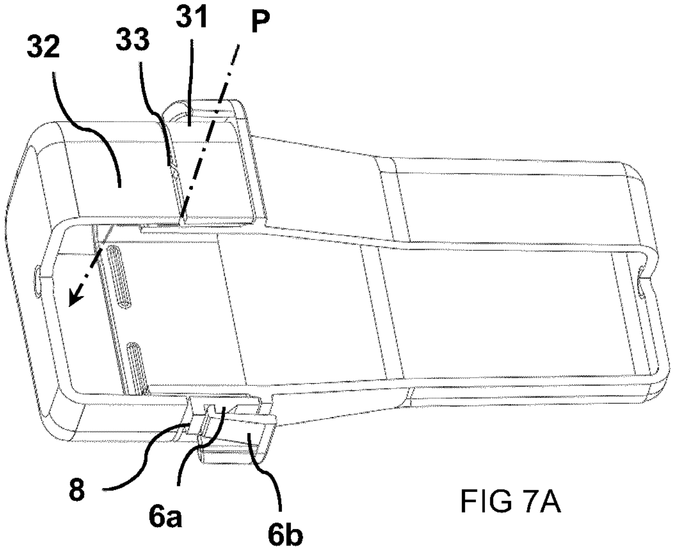
FIGS. 7A and 7B provide partial cross section perspective of a hard shell packaging product prior to and after opening.

FIG. 7A provides a partial cross section perspective view of a closed hard shell packaging product. A gas passage P that extends between cap and case allows gas access to an interior of the packaging product while in closed condition.

The interconnection member is configured to break by displacing the second cap part 32 with respect to the case 2 while retaining a coupled connection between the first cap part 31 and the case 2.

Figure 7B:
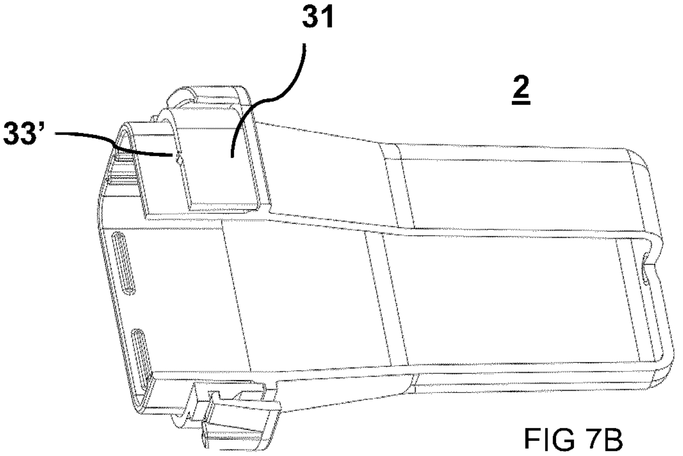

FIG. 7B provides a partial cross section perspective view a hard shell packaging product that has been opened after an initial closure by displacing the second cap part relative to the case, e.g. by pulling. Rather than disconnecting or opening the interlocked connection the pull force resulted in irreversible breakage of interconnection members 33'.

Breaking of the interconnection members 33' while retaining a connection between the case and the first cap part 31 not only provides a visual indication of opening the enclosure but also prevents re-closure of the case, e.g. by a new cap. Preferably, the single use interconnection means 6,6*a*,6*b* are further protected from tampering. In one embodiment, e.g. as shown in FIG. 7A, manual access to the interconnection means 6,6*a*,6*b* can be limited by providing a push member 8 that at least in part overlaps with the means for securing the first cap part to the case. Advantageously push member 8 can also provide a point of contact for an operator or machine grip to provide a force to assemble the cap onto the case. The grip or push member(s) therefore also protects the comparatively fragile interconnection members 33 between first and second parts 31,32 from damage during assembly of the cap onto the case. Advantageously, push member 8 prevents or at least hinders releasing the first cap part 31 form the case 2 because it limits access to the interlocked commotion between members 6*a* and 6*b* (See e.g. FIG. 7A).

Alternatively, or in addition, a label 6 (e.g. a self-adhesive label) may be provided that extends from the case across a boundary between the cap parts.

Figures 9A, 9B:
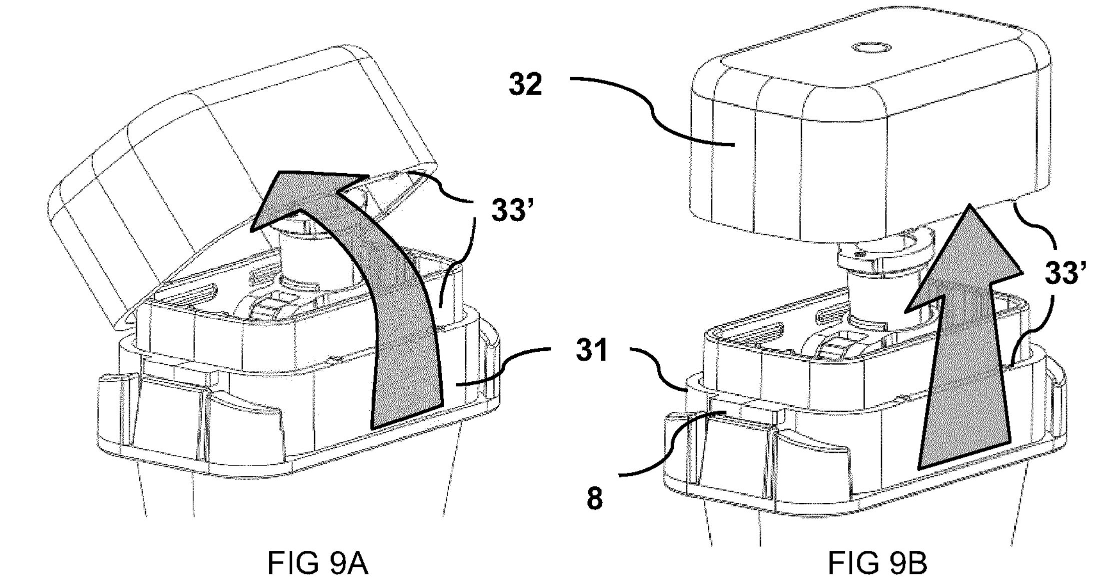
FIGS. 9A and 9B illustrate opening a packaged needle assembly.

FIGS. 9A and 9B further illustrate the process of opening by breaking the one or more interconnection members 33. As indicated in FIGS. 9A and 9B the packing product can be opened by an end-user who displaces the second cap part relative to the case. As indicated in FIG. 9B opening may involve a displacement of the second cap part relative to the case along an longitudinal axis of the case, e.g. by applying a pulling force onto the cap. In particular for embodiments having an essentially circular cross section (e.g. a described in relation to FIGS. 1-4) removal of the cap can may involve a rotational motion around the longitudinal axis, e.g. similar to an unscrewing motion of a bottle cap. Alternatively, or in addition, opening the packaging product may involve a rotation along a boundary between the first and second cap parts, e.g. as indicated in FIG. 9A.

Figure 10:
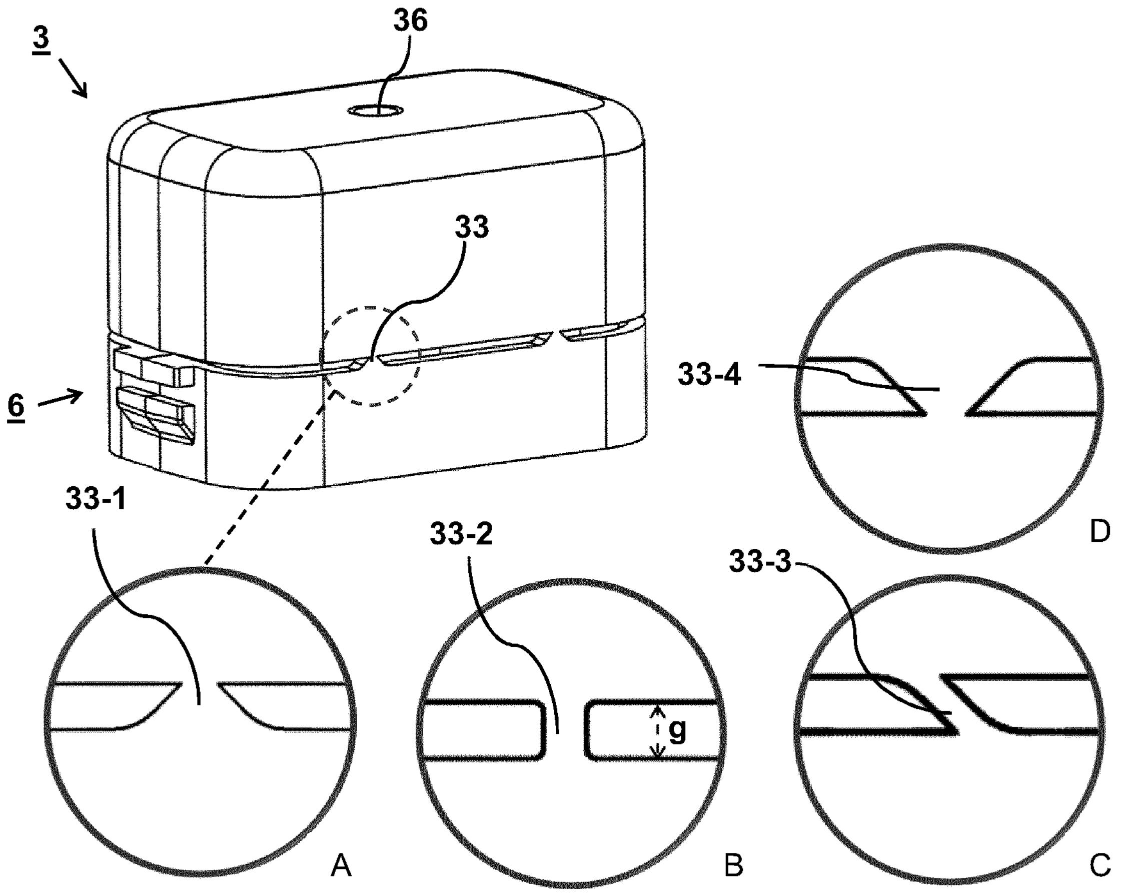
FIG. 10A-D illustrate aspects relating to cap parts of the hard shell packaging product.
Figure 11:
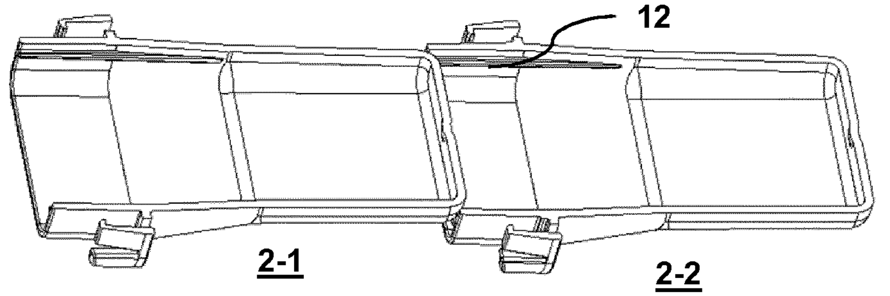
FIG. 11 illustrates aspects relating to case cap parts of the hard shell packaging product.

FIG. 10 illustrates aspects relating to the cap part of the hard shell packaging product. It will be appreciated that the interconnection members 33-1,33-2,33-3,33-4 can be embodied in various ways. In some embodiments, e.g. as shown under B the interconnection members can be regarded as essentially straight members that bridge a gap 'g' between first cap part 31 and the second cap part 32.

Alternatively the interconnection member 33 may be configured to comprise a tapered shape including a neck, e.g. as shown in 'A' and 'D'. The neck can advantageously define a break strength and location of brakeage, so that the visual marker of a broken connection (i.e. the remaining portion) can be directed predominantly at a specific cap part, e.g. the cap part that is not removed from the case. Alternatively, or in addition, the interconnection member 33 may comprise a slanting portion, e.g. as shown in 'C'. Each embodiment has been manufactured by injection moulding. Mark 36 indicates remnants of an entry point of a mould. In view of the flow direction embodiment D may be preferred.

In some embodiments, the case sidewall comprises a member, such as the ledge, a groove, or a magnet, etc. The ledge/member can advantageously provide grip for machine handling (e.g. a so-called auto feeder). FIG. 2B illustrates a case comprising an outwardly extending collar 25. The collar provides a face that enables automated handing of the case. Additionally, the casing is further preferably essentially free of protrusions and that extend beyond the ledge to allow rotational independent machine gripping.

Figure 12:
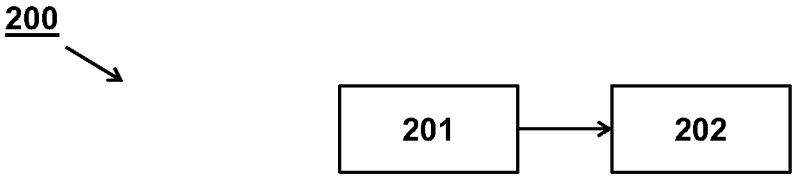
FIG. 12 schematically illustrated a packaging method.

Preferably, cap and case are further configured/dimensioned to prevent nesting of cases and/or nesting of caps. Nesting hinders automated packaging processes. To prevent nesting (also referred to as train-formation) case and/or cap can further comprise one or more member, e.g. a lip, that restricts formation of a flush contact areas between caps and/or cases. FIG. 12 depicts an embodiment wherein the case comprises an inwardly extending lip 12 that mitigates train assembly by preventing a bottom face of an adjacent case to extend into the case.

The case and cap as disclosed herein can be of particular benefit for packaging of products in a sterile package that is ready for direct use by an end user. The packaging product advantageously enables sterilizing the product in a package state while providing effective tamper protection by one or more of: members that provide a visual indication of an opening event and/or members that physically hinder tampering.

FIG. 12 illustrates a method of packaging a product, preferably a needle assembly. The method 200 comprises the steps of closing 201 a storage volume around a product to be packaged by coupling the case 2 and the cap 3 as disclosed herein. Advantageously, the method may comprise a step of 202 the packaged product to a gaseous disinfectant after coupling the cap and the case.

For the purpose of clarity and a concise description, features are described herein as part of the same or separate embodiments, however, it will be appreciated that the scope of the invention may include embodiments having combinations of all or some of the features described.

For example, In some embodiments, there is provided a packaged needle assembly product comprising: a hard-shell packaging product comprising a case and a cap arranged in an assembled configuration forming an enclosure for the needle assembly, and an adhesive label affixed to an outer face of the enclosure, wherein the label extends across at least a portion of a circumferential gap between an edge of the cap and an edge of the case thereby sealing the hard-shell packaging product, wherein the label includes a perforated section comprising a plurality of perforation lines that cross the gap under an angle (θ) from a first end that terminates at or beyond the edge of the cap to a second end that terminates at or beyond the edge of the case across the gap wherein the case and the cap are configured to slidingly engage to the assembled configuration, and wherein the case and the cap comprise circumferentially overlapping sidewall sections, and wherein the hard-shell packaging product comprises one or more radial channel that extends in a longitudinal direction between the overlapping sidewall sections to provide a gas passage to an interior of the enclosure.

In some embodiments the channel is at least in part defined by one or more protrusion extending outwardly from at least one of an inner face of a circumferentially overlapping wall section of the cap towards a corresponding overlapping wall section of the case, and an exterior face to the circumferentially overlapping wall section of the case towards a corresponding wall section of the cap.

In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. Where one claim refers to another claim, this may indicate synergetic advantage achieved by the combination of their respective features. But the mere fact that certain measures are recited in mutually different claims does not indicate that a combination of these measures cannot also be used to advantage. The present embodiments may thus include all working combinations of the claims wherein each claim can in principle refer to any preceding claim unless clearly excluded by context.

The invention claimed is:

1. A hard shell packaging product for a needle assembly comprising a canula extending from a hub for receiving a corresponding counterpart of a syringe, the hard shell product comprising:

a case extending in a longitudinal direction and a cap, wherein the case and the cap are configured to slidingly engage to an assembled configuration and form a closed condition for the hard shell product, in which closed condition the case and the can define an enclosed volume for storing the needle assembly, and wherein, in the closed condition, the case and the cap comprises circumferentially overlapping sidewall sections between which overlapping sidewall sections one or more radial channels extend in the longitudinal direction and are configured to form a gas passage between ambient and the enclosed volume, thereby enabling sterilization of the needle assembly with a gaseous agent, with the hard shell product in the closed condition and with the needle assembly stored in the enclosed volume.

2. The hard shell product according to claim 1, comprising one or more single use securing members for securing the cap to the case.

3. The hard shell packaging product according to claim 2, wherein the one or more single use securing members for securing the cap to the case comprises a label extending circumferentially across a boundary between the cap and the case.

4. The hard shell packaging product according to claim 3, wherein the label comprises a plurality of perforation lines that extend across the boundary between the cap and the case.

5. The hard shell product according to claim 1, wherein the cap comprises:

at least a first cap part comprising one or more securing members for securing the first cap part to the case; and a second cap part that is connected to the first cap part by one or more interconnection members configured to break by displacing the second cap part with respect to the case while retaining a coupled connection between the first cap part and the case.

6. The hard shell packaging product according to claim 5, wherein the one or more securing members for securing the first cap part to the case comprise interlocking elements configured to snap into a locked position.

7. The hard shell packaging product according to 5, wherein each of: the one or more interconnection members, and the one or more securing members for securing the first cap part to the case, are configured to break at a force smaller than a snap out force for releasing the interlocking elements from the locked position.

8. The hard shell packaging product according to claim 5, wherein the first cap part comprises one or more outwardly extending push members.

9. The hard shell packaging product according to claim 8, wherein the one or more push members at least partly overlaps the one or more securing members for securing the first cap part to the case.

10. The hard shell packaging product according to claim 5, wherein one or more of the case and the second cap part comprise members for external manual grip for displacing the second cap part with respect to the case.

11. The hard shell packaging product according to claim 1, wherein the one or more radial channels are at least in part defined by one or more protrusions extending outwardly from at least one of an inner face of the circumferentially overlapping wall section of the cap towards a corresponding overlapping wall section of the case, and an exterior face to the circumferentially overlapping wall section of the case towards a corresponding wall section of the cap.

12. The hard shell packaging product according to claim 1, wherein the case comprises one or more engagement faces configured to engage with one or more faces of the needle assembly, to restrict rotational freedom of the needle assembly along the longitudinal direction.

13. The hard shell packaging product according to claim 1, wherein an internal sidewall of the case comprises one or more retention members that engage with the needle assembly to restrict displacement of the needle assembly along the longitudinal direction.

14. The hard shell packaging product according to claim 1, wherein the case has an exterior section that is essentially circular and free of protrusions and that is bound by an outwardly extending ledge.

15. The hard shell packaging product according to claim 1, wherein the case further comprises one or more lips that restrict formation of a flush contact areas between exterior and interior faces of stacked cases.

16. A cap and a case for assembly into the hard shell packaging product according to claim 1, wherein the cap extends in a longitudinal direction, and wherein the cap and case, when in a coupled configuration, define an enclosure for a product to be stored, wherein:

the case and cap are configured to, in the coupled configuration, provide circumferentially overlapping sidewall sections, with one or more radial channels extending in the longitudinal direction between the overlapping sidewall sections, the one or more radial channels being configured to form a gas passage between ambient and the enclosure, and thereby to enable sterilization of the product with a gaseous agent with the case and the cap in the coupled configuration and with the product stored in the enclosure.

17. The cap and a case according to claim 16, wherein:

the cap comprises:

at least a first cap part comprising one or more securing members for the securing the first cap part to the case; and a second cap part that is connected to the first cap part by one or more interconnection members configured to break by displacing the second cap part with respect to the case while retaining a coupled connection between the first cap part and the case.

18. A packaged needle assembly comprising a needle assembly and the packaging product according to claim 1, wherein the needle assembly comprises a canula and a hub, and wherein the packaging product is in the closed condition with the needle assembly being stored in said enclosed volume defined by the case and the cap.

19. The packaged needle assembly according to claim 18, wherein the needle assembly further comprises a needle guard.

20. A method of packaging a product, comprising closing a storage volume around a product to be packaged by coupling the-and-the cap and the case for assembly according to claim 16 and/or exposing the product to a gaseous disinfectant after coupling the cap and the case.

* * * * *